United States Patent
Dallerup Rasmussen et al.

(10) Patent No.: US 12,414,534 B2
(45) Date of Patent: Sep. 16, 2025

(54) CONTROL UNIT AND A CONFIGURATION TAG OF A MILK ANALYSIS APPARATUS

(71) Applicant: DELAVAL HOLDING AB, Tumba (SE)

(72) Inventors: Claus Dallerup Rasmussen, Tumba (SE); John Slaaby, Tumba (SE)

(73) Assignee: DeLaval Holding AB, Tumba (SE)

(*) Notice: Subject to any disclaimer, the term of this patent is extended or adjusted under 35 U.S.C. 154(b) by 557 days.

(21) Appl. No.: 17/618,711

(22) PCT Filed: Jun. 9, 2020

(86) PCT No.: PCT/SE2020/050582
§ 371 (c)(1),
(2) Date: Dec. 13, 2021

(87) PCT Pub. No.: WO2020/251456
PCT Pub. Date: Dec. 17, 2020

(65) Prior Publication Data
US 2022/0295734 A1    Sep. 22, 2022

(30) Foreign Application Priority Data
Jun. 14, 2019  (SE) .................................. 1950715-1

(51) Int. Cl.
*A01J 5/007*   (2006.01)
*G01N 33/04*   (2006.01)
*G01N 35/00*   (2006.01)

(52) U.S. Cl.
CPC .............. *A01J 5/007* (2013.01); *G01N 33/04* (2013.01); *G01N 35/00871* (2013.01)

(58) Field of Classification Search
CPC ........ A01J 5/007; A01J 5/0131; G01N 33/04; G01N 35/00871; G01N 33/48792; G01N 35/00722
See application file for complete search history.

(56) References Cited

U.S. PATENT DOCUMENTS

2009/0255473 A1   10/2009  Katz et al.
2009/0309730 A1*  12/2009  Kothari .............. G03G 15/5075
                                                    340/572.1
(Continued)

FOREIGN PATENT DOCUMENTS

CN        104186352    12/2014
EP        2 503 876    10/2012
(Continued)

OTHER PUBLICATIONS

Search Report for SE Application No. 1950715-1 dated Jun. 14, 2019, 2 pages.
(Continued)

Primary Examiner — Thomas C Lee
Assistant Examiner — Tyler Dean Hedrick
(74) Attorney, Agent, or Firm — NIXON & VANDERHYE

(57) ABSTRACT

A control unit (240) and configuration tag (125) of a milk analysis apparatus (120) includes a first wireless communication device (310), for communication with a memory device (330) of the configuration tag. The configuration tag is applicable to the milk analysis apparatus and includes a reference sign (115) of a milk extracting arrangement (110) to which the milk analysis apparatus is intended to work in conjunction with. The communication is made via a second wireless communication device (320) comprised in the configuration tag. The control unit (340) is configured to retrieve, via the first wireless communication device, configuration data of the milk extracting arrangement that the milk analysis apparatus is intended to operate in conjunction with, from the memory device of the configuration tag; and to configure the control unit, based on the retrieved configuration data of the milk extracting arrangement.

22 Claims, 4 Drawing Sheets

(56) References Cited

U.S. PATENT DOCUMENTS

| | | | |
|---|---|---|---|
| 2017/0228567 A1* | 8/2017 | Holleman | ............... B23B 49/00 |
| 2019/0122015 A1* | 4/2019 | Huang | ............... G06K 7/10356 |
| 2019/0147202 A1* | 5/2019 | Harney | ............... H04L 41/0809 |
| | | | 235/375 |
| 2020/0121545 A1* | 4/2020 | Parker, Sr. | ........... A61H 9/0078 |
| 2022/0110290 A1* | 4/2022 | De Groot | ........... G05B 19/4155 |

FOREIGN PATENT DOCUMENTS

| | | |
|---|---|---|
| WO | 2011/126432 | 10/2011 |
| WO | 2015/001540 | 1/2015 |
| WO | 2016/053105 | 4/2016 |
| WO | 2017/144913 | 8/2017 |
| WO | 2018/236271 | 12/2018 |

OTHER PUBLICATIONS

International Search Report for PCT/SE2020/050582 dated Sep. 10, 2020, 2 pages.
Written Opinion of the ISA for PCT/SE2020/050582 dated Sep. 10, 2020, 5 pages.

* cited by examiner

CONTROL UNIT AND A CONFIGURATION TAG OF A MILK ANALYSIS APPARATUS

This application is the U.S. national phase of International Application No. PCT/SE2020/050582 filed 9 Jun. 2020, which designated the U.S. and claims priority to SE Patent Application No. 1950715-1 filed 14 Jun. 2019, the entire contents of each of which are hereby incorporated by reference.

TECHNICAL FIELD

This document discloses a control unit of a milk analysis apparatus and a configuration tag, applicable to the milk analysis apparatus. More particularly, it is herein presented a control unit of a milk analysis apparatus comprising a first wireless communication device, for communication with a memory device of a configuration tag which is applicable to the milk analysis apparatus and comprises a reference sign of a milk extracting arrangement to which the milk analysis apparatus is intended to work in conjunction with, wherein the communication is made via a second wireless communication device comprised in the configuration tag.

BACKGROUND

On an animal farm, it is important to keep the animals healthy in order to enhance milk/meat production, and/or to monitor when animals are in heat and/or pregnant, for example. It is important to inseminate animals at an optimal moment in order to successfully fertilise the animal. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance of the animal may be estimated (based on urea).

Thereby, a farmer is provided with important information concerning status of each individual animal. However, to perform and analyse biomarker measurements of all individual animals at a farm, e.g. by applying milk samples on prepared dry sticks, and analyse these samples are time consuming for the farmer, who may have to take care of various other important issues. It also put high demands on administrative skills on the farmer to distinguish biomarker measurements from different animals; to keep track on when it is time to repeat the biomarker measurement for each individual animal and when to change biomarker measurement units; maintenance of the biomarker test equipment as well as high demands on cleanliness for not allowing a biomarker measurement of a first animal to be contaminated by biological matters of another animal.

A milk analysis apparatus may be arranged to cooperate with a milk extracting arrangement, for regularly analysing milk samples of the animals, e.g. at or around the moment of a milking session. The milk analysis apparatus may extract a milk sample and provide it on a milk analysis unit such as a dry stick/lateral flow stick/lateral flow test strip or similar. The milk is typically diluted with a diluent, which also may be used to rinse the tubings between test sessions. The diluent may be provided in a liquid container.

The milk analysis units are maintained in a cassette, for example on a tape in the cassette as disclosed in document WO 2018236271. Thereby milk analysis units may be easily administrated at the farm by forwarding one milk analysis unit at the time. One milk analysis unit is typically used for each test sample. The cassette may comprise a large amount of milk analysis units, yet the cassette with the milk analysis units has to be exchanged for a new one when all the milk analysis units have been consumed.

The farm may comprise several milk extracting arrangements such as milking robots, each of them being provided with a separate milk analysis apparatus.

It would be desired to find a solution for assisting the farmer in configuring the respective milk analysis apparatus to work in conjunction with the associated milk extracting arrangement.

SUMMARY

It is therefore an object of this invention to solve at least some of the above problems and facilitate for a farmer to measure a biomarker value of a milk sample of an animal.

A biomarker, or biological marker, generally refers to a measurable indicator of some biological state or condition of the animal. The biomarker value measurement may be associated with pregnancy/reproduction of the animal, health of the animal, and/or quality of the milk of the animal.

According to a first aspect of the invention, this objective is achieved by a control unit of a milk analysis apparatus, in an agricultural environment. The milk analysis apparatus comprises a first wireless communication device, for communication with a memory device of a configuration tag which is applicable to the milk analysis apparatus. The configuration tag comprises a reference sign of a milk extracting arrangement to which the milk analysis apparatus is intended to work in conjunction with. The reference sign is a visual marker such as e.g. an integer, a letter, a geometric shape, a colour, a string of letters, etc., that corresponds to the intended milk analysis apparatus. The communication is made via a second wireless communication device comprised in the configuration tag. The control unit is configured to retrieve configuration data of the milk extracting arrangement that the milk analysis apparatus is intended to operate in conjunction with, from the memory device of the configuration tag via the first wireless communication device. Also, the control unit is configured to configure the control unit, based on the retrieved configuration data of the milk extracting arrangement.

Thereby, by pre-storing and maintaining configuration data of the milk extracting arrangement in the memory device of the configuration tag, the configuration process of the farmer is reduced to applying the configuration tag preconfigured with the configuration data of the relevant milk extracting arrangement, to the milk analysis apparatus. Hereby costs, maintenance and work intensity of the farmer associated with management of the milk analysis apparatus is minimised or at least reduced.

In a first possible implementation of the control unit according to the first aspect wherein the retrieved configuration data comprises a reference indicator corresponding to the reference sign of the configuration tag. The reference indicator is a digital correspondence to the externally applied reference sign of the configuration tag, stored in a memory device of the configuration tag. The control unit may be configured to check whether the retrieved reference indicator corresponds to the milk extracting arrangement to which the milk analysis apparatus currently works in conjunction with. The control unit may also be configured to either deactivate the first wireless communication device when the reference indicator corresponds to the milk extracting arrangement; or re-configure the control unit to work in conjunction with the milk extracting arrangement as indicated by the retrieved reference indicator.

The control unit may thereby check whether the configuration tag has been exchanged or not and make a reconfiguration when it is detected that a new configuration tag has been applied to the milk analysis apparatus.

In a second possible implementation of the control unit according to the first aspect, or according to the first implementation thereof, the retrieved configuration data may comprise a network location reference to the milk extracting arrangement.

It then becomes possible for the control unit to obtain the relevant network location reference of the milk extracting arrangement without requiring any additional intervention or manual input by the farmer. Hereby time is saved, and the risk of misprinting the network location reference is omitted.

In a third possible implementation of the control unit according to the first aspect, or according to any previously disclosed implementation thereof, the retrieved configuration data may comprise a network location reference to a data resource, from which additional configuration data related to the milk extracting arrangement is retrievable.

It thereby becomes possible for the control unit to obtain additional information of the milk extracting arrangement from a data resource without requiring any additional intervention or manual input by the farmer. Hereby time is saved, and the risk of misprinting the network location reference of the data resource is omitted.

In a fourth possible implementation of the control unit according to the first aspect, or according to any previously disclosed implementation thereof, the control unit may also be configured to temporarily re-activate the first wireless communication device at a predetermined time interval; and/or to deactivate the first wireless communication device when having retrieved the configuration data from the memory device of the configuration tag.

By deactivating the wireless communication devices when they are not required to be used and only activate them for a brief time period when information exchange between the control unit and the configuration tag is desired, energy is saved. Also, signal interference with other close-by devices capable of wireless signalling is eliminated, or at least reduced.

According to a second aspect of the invention, this objective is achieved by a configuration tag. The configuration tag is applicable to a milk analysis apparatus. The configuration tag comprises a memory device which in turn comprises a reference sign corresponding to a milk extracting arrangement to which the milk analysis apparatus is intended to work in conjunction with. Also, the configuration tag comprises a second wireless communication device, configured for communication with a control unit of the milk analysis apparatus via a first wireless communication device of the milk analysis apparatus. The memory device is configured to provide configuration data of the milk extracting arrangement that the milk analysis apparatus is intended to operate in conjunction with, to the control unit of the milk analysis apparatus, via the second wireless communication device.

Thereby, by pre-storing and maintaining configuration data of the milk extracting arrangement in the memory device of the configuration tag, the configuration process of the farmer is reduced to apply the configuration tag preconfigured with the configuration data of the relevant milk extracting arrangement, to the milk analysis apparatus.

Hereby costs, maintenance and work intensity of the farmer associated with management of the milk analysis apparatus is minimised or at least reduced.

In a first possible implementation of the configuration tag according to the second aspect, the memory device may also be configured to provide a reference indicator corresponding to the reference sign of the configuration tag, to the control unit of the milk analysis apparatus, via the second wireless communication device.

The configuration tag may thereby provide the prestored reference indicator of the configuration tag to the control unit of the milk analysis apparatus, which corresponds to the external reference sign of the configuration tag. The farmer may thus with a minimum of effort configure/reconfigure the control unit of the milk analysis apparatus by selecting and apply a configuration tag having a reference sign corresponding to the relevant milk extracting arrangement.

In a second possible implementation of the configuration tag according to the second aspect, or any of the possible implementations thereof, the memory device may be configured to provide configuration data comprising a network location reference to the milk extracting arrangement.

It then becomes possible to provide the relevant network location reference of the milk extracting arrangement without requiring any additional intervention or manual input by the farmer. Hereby time is saved, and the risk of misprinting the network location reference is omitted.

In a third possible implementation of the configuration tag according to the second aspect, or any of the possible implementations thereof, the memory device may be configured to provide configuration data comprising a network location reference to a data resource, from which additional configuration data related to the milk extracting arrangement is retrievable.

It then becomes possible to provide the relevant network location reference of the milk extracting arrangement without requiring any additional intervention or manual input by the farmer. Hereby time is saved, and the risk of misprinting the network location reference is omitted.

According to a third aspect of the invention, this objective is achieved by a system in an agricultural environment. The system comprises a control unit according to the first aspect, or any of the possible implementations thereof. Further, the system also comprises a configuration tag according to the second aspect, or any of the possible implementations thereof.

In addition, the system comprises a milk analysis apparatus comprising a first wireless communication device, for communication with a memory device of the configuration tag via a second wireless communication device comprised in the configuration tag. The system comprises a milk extracting arrangement, operating in conjunction with the milk analysis apparatus.

Thereby, by pre-storing and maintaining configuration data of the milk extracting arrangement in the memory device of the configuration tag, the configuration process of the farmer is reduced to apply the configuration tag preconfigured with the configuration data of the relevant milk extracting arrangement, to the milk analysis apparatus.

Hereby costs, maintenance and work intensity of the farmer associated with management of the milk analysis apparatus is minimised or at least reduced.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a control unit and a configuration tag, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
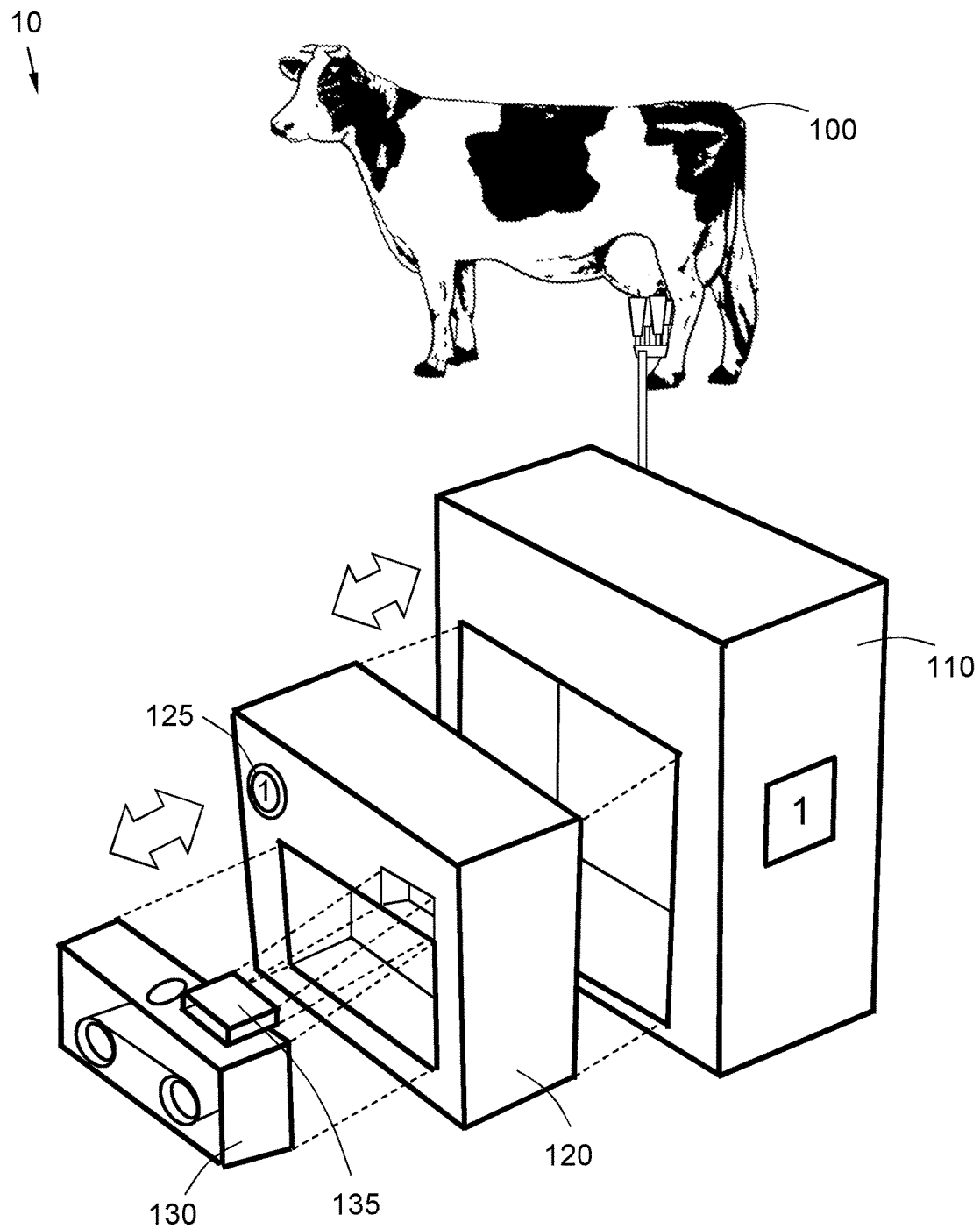
FIG. 1 illustrates an example of an arrangement for measuring a biomarker value of a milk sample of an animal.

FIG. 1 illustrates a scenario with a system 10 for analysing milk of an animal 100 which may be comprised in a herd of dairy animals at a dairy farm.

"Animal" may be any arbitrary type of domesticated female milk producing and/or meat producing mammal such as cow, goat, sheep, horse, camel, primate, dairy buffalo, donkey, yak, etc.

Milk of the animal 100 may be extracted by a milk extracting arrangement, or milking equipment 110 such as e.g. a milking robot or other milking arrangement and provided to a milk analysis apparatus 120.

The milk analysis apparatus 120 may be associated with and possibly even releasably insertable into the milk extracting arrangement 110 in some embodiments. Thus, there may be an interface between the milk extracting arrangement 110 and the milk analysis apparatus 120 for providing milk and possibly also electricity via the milk extracting arrangement 110 to the milk analysis apparatus 120.

The milk analysis apparatus 120 comprises various electronics and equipment such as a camera, one or several pumps, a tube element for attachment to the interface to the milk extracting arrangement 110, motors, a communication unit etc.

A cassette 130 may be detachably inserted into the milk analysis apparatus 120. The cassette 130 may comprises a tape or similar corresponding arrangement with milk analysis units such as dry sticks/lateral flow sticks/lateral flow test strips or similar. The milk analysis units are configured to indicate a biomarker value of a milk sample of the animal 100, e.g. indicate progesterone in the milk sample by a lateral flow test, when a milk sample is applied to the milk analysis unit.

The cassette 130 may in some embodiments be configured to be detachably inserted in the milk analysis apparatus 120 and held in place by a fastening means such as a snap lock, a magnet, a screw, etc., and a door of the milk analysis apparatus 120 may be closed for enclosing the cassette 130 within the milk analysis apparatus 120, thereby further fixating the cassette 130 in the position. It is thereby easy for the farmer to exchange the cassette 130 when all the milk analysis units are consumed, yet the cassette 130 is well protected from the harsh surroundings in an agricultural environment.

Also, a liquid container 135 may be insertable into, or associated with (i.e. physically connected to) the milk analysis apparatus 120. The liquid container 135 may comprise a diluent, which may be used to dilute the extracted milk and also, or alternatively, to rinse the tubing, needle, pump etc., of the milk analysis apparatus 120.

The tubing, needle, pump etc. may be kept in a dosing module. Thereby, the tubing, needle, and pump may be replaced all at the same time in one single replacement.

Thereby, a milk sample of the animal 100 may be extracted from the animal 100 by the milk extracting arrangement 110 and provided via the milk analysis apparatus 120 to one of the milk analysis units on the tape of the cassette 130. The milk analysis units may react on presence and/or amount of one or several biomarkers, e.g. by changing colours, or intensity of a colour. The camera in the milk analysis apparatus 120 may capture an image through an opening of the cassette 130. The captured image of the milk analysis unit may then be analysed by a control unit, and based on the intensity of the colour, presence and/or quantity of the biomarker in the milk sample may thereby be determined.

The measured biomarker may be e.g. progesterone, glycoprotein, oestrogen and/or Gonadatropin-Releasing Hormones, or any other similar biomarker associated with reproduction or health of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrous and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the farmer to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the farmer may subscribe to a cassette 130 comprising a certain milk analysis units configured to measure a biomarker, or a set of biomarkers, as selected by the farmer; and/or different cassettes 130 comprising milk analysis units, e.g. on the tape configured to measure different biomarkers, or sets of biomarkers, during different periods of time of the year.

Thus, the milk analysis apparatus 120 comprises several modules such as the cassette 130, the dosing module and/or the liquid container 135, which are to be changed for a new respective module at particular time intervals, which may occur at different moments in time for the different modules.

The cassette 130 with the milk analysis units is to be exchanged when the milk analysis units have been consumed. However, the number of used milk analysis units will be dependent on how often sampling is made, how many milk analysis units that are used for each animal 100 and/or how many defect milk analysis units there are in the cassette 130. For example, in case the farmer is primarily interested in timing insemination of the animal 100, samples of that animal 100 may be taken only around, or right before, a moment in time when it is predicted that the particular animal 100 is in heat. Animals 100 such as cows and heifers typically go into heat or oestrus every 17 to 24 days (in average 21 days), why the next heat could be roughly predicted based on knowledge of the moment in time of the last heat.

Another farmer may want to take a milk sample on every milking event, e.g. in order to survey health status of a particular animal 100. Also, different cassettes 130 may possibly comprise a different number of milk analysis units. The time period between exchange of the cassettes 130, dosing modules and/or liquid containers 135 for different milk analysis apparatuses 120 may thereby be different.

The dosing module comprises one or several pumps, such as hose pumps and a tube element for attachment to the milk extracting arrangement 110. The one or several pumps may be configured to act on the tube element for advancing the milk sample from the milk extracting arrangement 110 through the tube element to a needle. The milk sample may then be diluted with diluent from the liquid container 135 in a mixing chamber of the needle (or possibly in a separate mixing chamber and then provided to the needle), where after the diluted milk sample may be applied from the needle to the milk analysis unit of the cassette 130.

The various modules, i.e. the dosing module, the liquid container 135 and/or the cassette 130 may comprise fastening means, e.g. in form of a snap fit arrangement, magnetics, screw joints, etc., arranged to attach the respective module onto the milk analysis apparatus 120.

The modular structure of the provided solution has several advantages. By keeping the arrangement modular in form of the dosing module, the liquid container 135 and the cassette 130, which may be attached to milk extracting arrangement 110 of the farm; costs, maintenance and work intensity of the farmer may be minimised or at least reduced. Also, by separating the consumable material such as milk analysis units/measurement sticks of the cassette 130, from elements subject to wear, like the pumps of the dosing module, and the electronics and instruments of the milk analysis apparatus; the cassette 130 could be continuously replaced with another replacement cassette e.g. ordered via a courier service or postal office subscription.

The milk analysis apparatus 120 may on the other hand be detached from the milk extracting arrangement 110 and the dosing module/liquid container 135/cassette 130 upon malfunction and sent to a workshop for troubleshooting, repair, maintenance, etc.

Meanwhile, an identical replacement milk analysis apparatus 120 may be provided to the farm, enabling continuous biomarker measurements on the farm, also when the equipment of the milk analysis apparatus 120 is malfunctioning, to which the old dosing module/liquid container 135/cassette 130 could be applied.

Further, the described arrangement may be operated by the farmer without requiring a particularly trained technician to come and visit the farm. Instead, the farmer may send the malfunctioning module to the workshop; or just replace it.

By maintaining the diluent, the milk analysis units and the tubings, respectively, in separate modules, they are protected from any possible affection of the environment at the farm.

However, an appearing problem is that it may become problematic for the farmer to keep track on which milk analysis apparatus 120 to configure and use for the different milk extracting arrangements 110 when the farm comprises a large number of milk extracting arrangements 110.

On some farms, there may be more milk extracting arrangements 110 than milk analysis apparatus 120, for example, and the milk analysis apparatus 120 may be changed between different milk extracting arrangements 110.

A configuration tag 125 is introduced for this reason, comprising a memory device wherein configuration data is stored, corresponding to the milk extracting arrangement 110 and/or a reference indicator to the milk extracting arrangement 110. The configuration tag 125 may also comprise an external reference sign 115 of the milk extracting arrangement 110 to which the milk analysis apparatus 120 is intended to work in conjunction with.

Hereby, it becomes very easy for the farmer to configure the milk analysis apparatus 120 and to keep track of the milk analysis apparatus 120/milk extracting arrangement 110 combination.

Figure 2A:
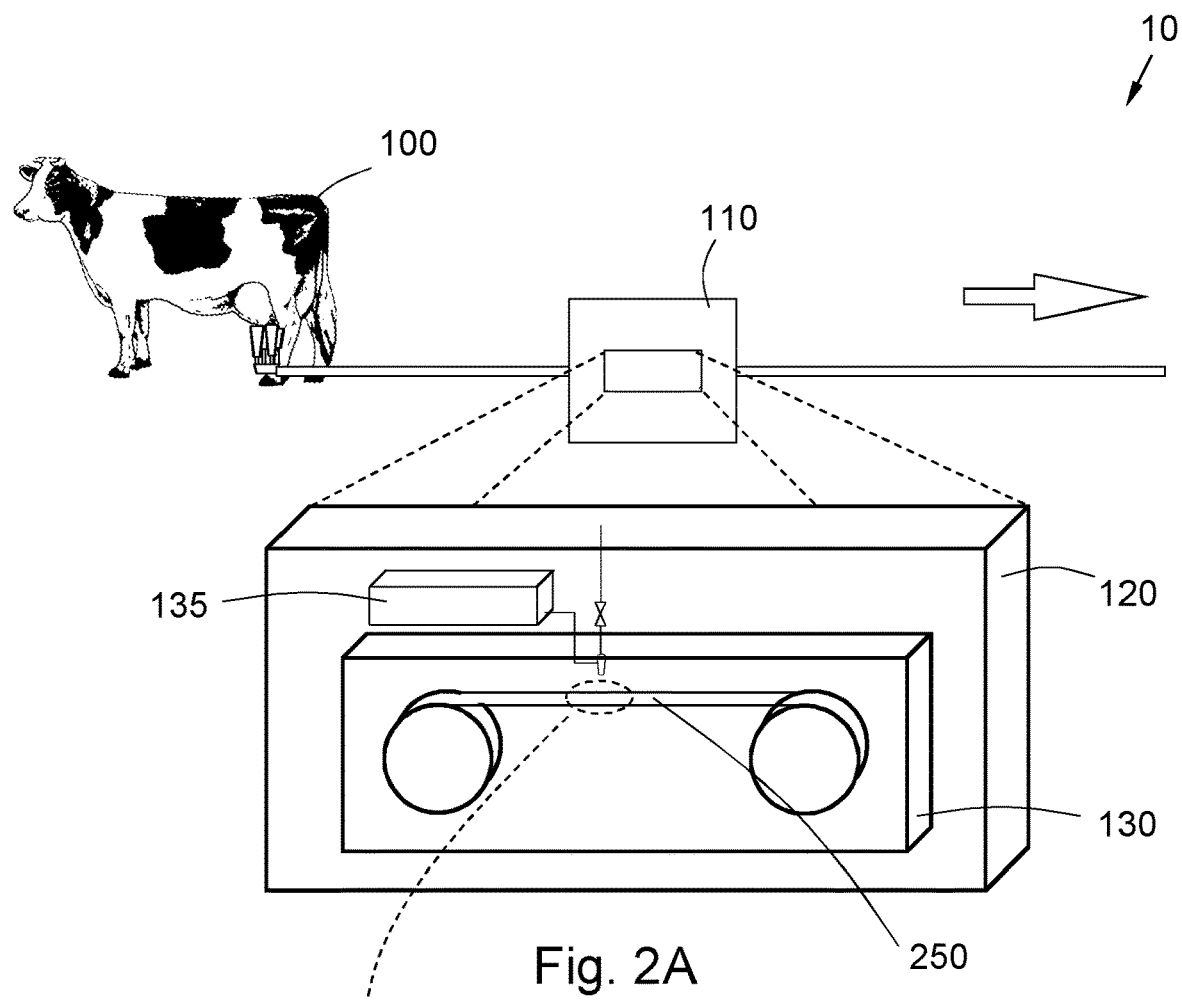
FIG. 2A illustrates a cassette inserted into a milk analysis apparatus, according to an embodiment.

FIG. 1 and FIG. 2A depict general overview of the environment in which the milk extracting arrangements 110, the milk analysis apparatus 120, the cassette 130, the liquid container 135, and the dosing module according to the provided solution is intended to operate, without going too much into details, in order for the reader to get a rough overview. Sublime examples of details of the tape may be studied in FIG. 2B. FIG. 3A illustrates a particular aspect of the provided solution while FIG. 3B presents details of the disclosed solution.

Figure 2B:
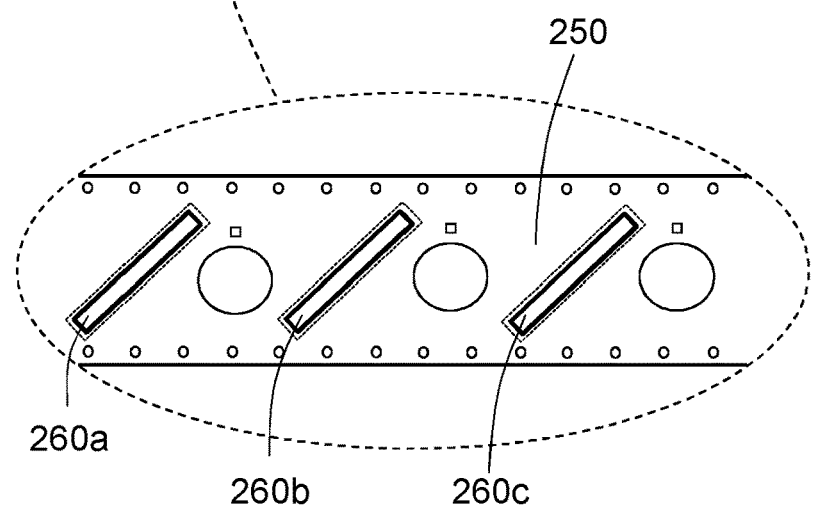
FIG. 2B illustrates a section of a tape comprising dry sticks, according to an embodiment.
Figure 3A:
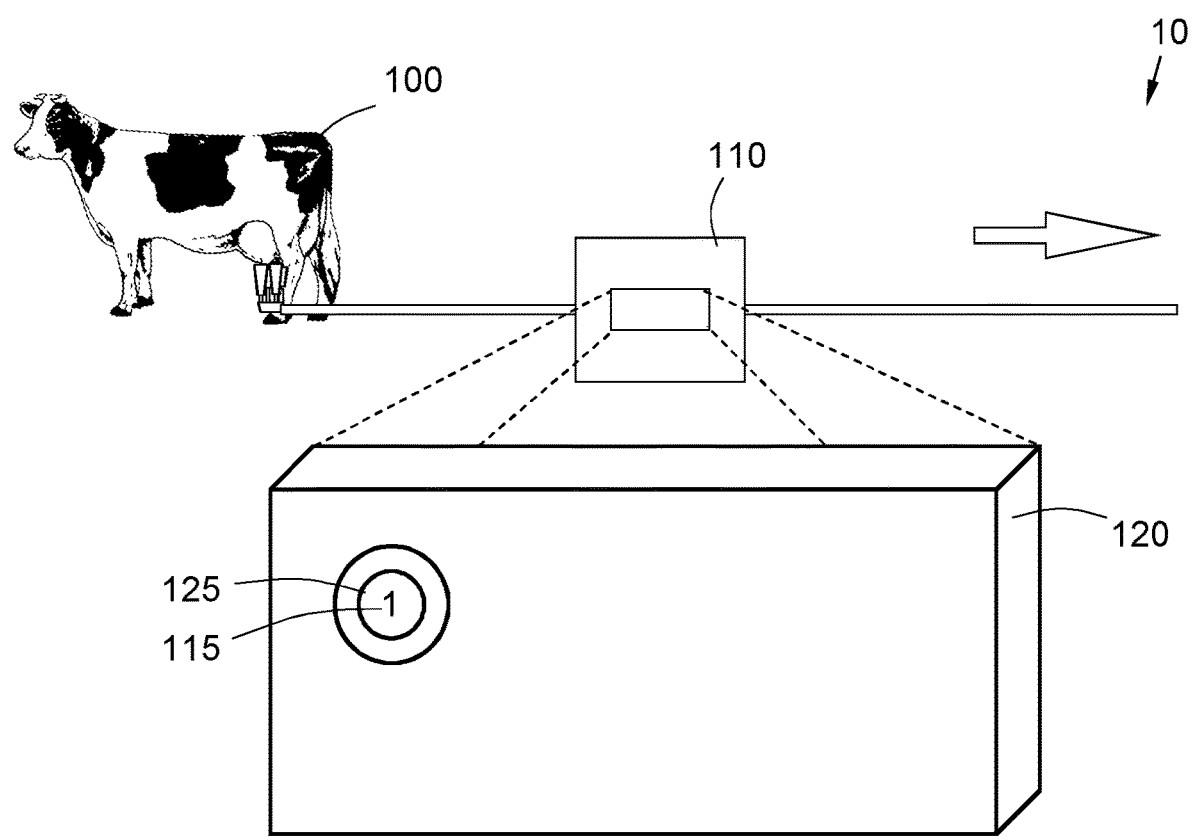
FIG. 3A illustrates the configuration tag and the milk analysis apparatus, according to an embodiment.
Figure 3B:
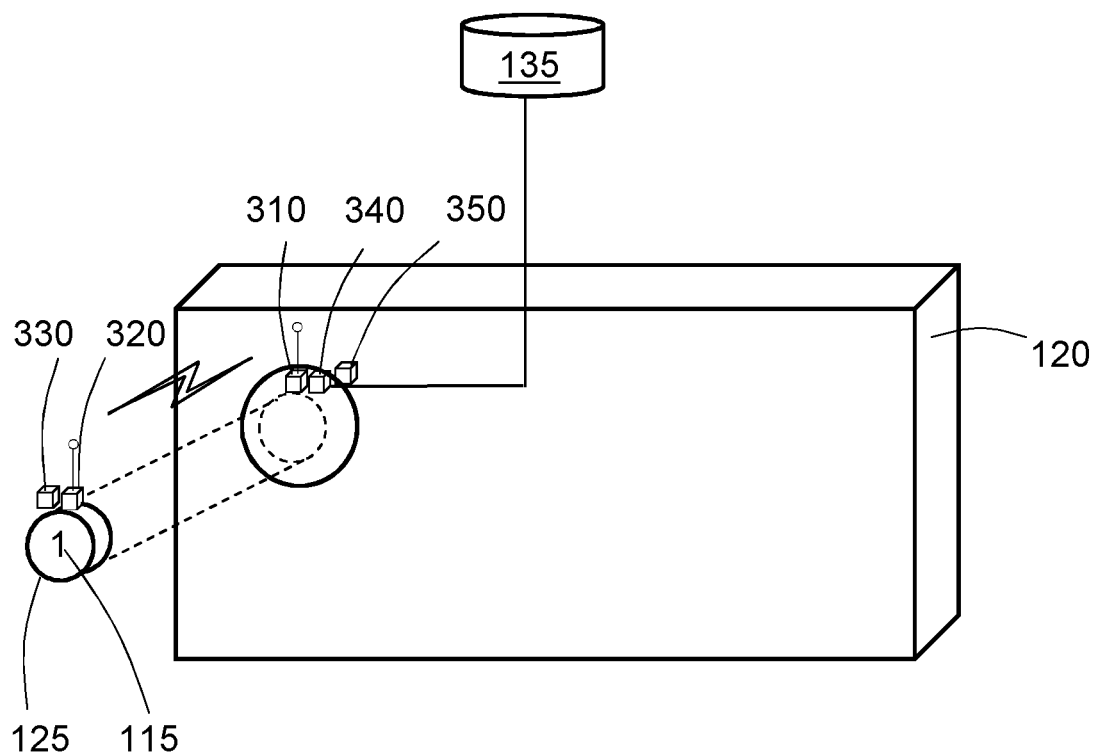
FIG. 3B illustrates the configuration tag and the milk analysis apparatus, according to an embodiment.

FIGS. 2A and 2B illustrate a scenario illustrating a milk analysis apparatus 120, a cassette 130, a liquid container 135 and a dosing module interacting with each other and with the milk extracting arrangement 110, according to an embodiment.

The milk analysis apparatus 120 may comprise electronics and equipment such as e.g. a camera, a tube element for attachment to the milk extracting arrangement 110, a motor, a communication unit, etc., to be used for determining a biometric value of a milk sample received from an animal 100. In some embodiments, one or several pumps and tubings are comprised in the dosing module. The pump/s is configured to act on the tube element for advancing the milk sample from the milk extracting arrangement 110 through the tube element to reach the needle; or the mixing chamber of the needle. The mixing chamber may alternatively be external to the needle. The tube elements are configured to receive the milk sample of the animal 100 via a milk extracting arrangement 110 and provide the milk sample to a needle, i.e. the needle comprised in the dosing module.

In the illustrated embodiment, the dosing module may comprise a needle for applying the milk sample to a milk analysis unit 260a, 260b, 260c on a tape 250 in the cassette 130 through an opening in the cassette 130. The camera may then align the needle with the milk analysis unit 260a, 260b, 260c on the tape 250 of the cassette 130, in an embodiment. The milk analysis units 260a, 260b, 260c may not necessarily be kept on a tape 250, but other similar solutions may be applied wherein the milk analysis units 260a, 260b, 260c may be maintained on another similar substrate.

The cassette 130 may comprise a known number of milk analysis units 260a, 260b, 260c such as e.g. 400, or 500, etc.

The milk analysis units 260a, 260b, 260c may for example comprise individually sealed lateral flow sticks. The lateral flow sticks may be arranged to indicate a biomarker in the milk sample of the animal 100 when a lateral flow test is performed. The lateral flow sticks may comprise a sample pad with antibody treated gold particles which are dispersed into the milk sample when applied onto the sample pad and an absorbent pad for receiving a capillary flow of the milk sample, from the sample pad. The absorbent pad in turn may comprise a test line treated with a biomarker reference which binds antibody treated gold particles of the milk sample and thereby brings the test line to change colour when exposed for milk comprising a biomarker level lower than a threshold limit. The absorbent pad may also comprise a control line treated with an antibody reference which binds antibody treated gold particles of the milk sample regardless of the progesterone level in the milk, and thereby brings the control line to change colour when exposed for milk comprising antibody treated gold particles.

The dosing module may also comprise a liquid evacuator or drainage, which may collect liquid that has been output by the needle. The liquid, when comprising merely milk, may be returned back to the milk line/milk extracting arrangement 110 in some embodiments. In other embodiments, when the milk has been mixed with diluent, the liquid may be conveyed away from the cassette 130 in order not to soak or contaminate other, unused, milk analysis units 260a, 260b, 260c of the tape 250 on the cassette 130.

The camera may capture an image of the milk analysis unit 260a, 260b, 260c of the carrier tape 250 through the opening, and based on these images, a cassette external motor may adjust the tape 250 for positioning a new milk analysis unit 260a, 260b, 260c, on which a new test is to be made, in relation to the needle.

The milk analysis apparatus 120 may also comprise a communication device which may communicate via a wired or wireless communication interface with an output unit, a database, a communication device of a farmer, etc.

The control unit may be configured to determine a biomarker value of the milk sample of the animal 100, based on an analysis of the image, captured by the camera. The control unit may be comprised in the milk analysis apparatus 120 in some embodiments; or be external to the milk analysis apparatus 120.

A database may store measured biometric values of the animal 100, associated with an identity reference of the animal 100 and/or a time stamp of the measurement. Other measurements and/or data related to the animal 100 may also be stored in the database, such as milk yield, e.g. measured by the milk flow meter, activity, breed, parity, rumination, lactation, resting, feed intake, energy balance, Days In Milk, milk production, age and possibly other similar animal status related parameters.

When a deviation, exceeding a first threshold limit, is detected between the outcomes of the biomarker measurement and the corresponding reference value, an alert may be outputted to the farmer or other responsible person. The alert may comprise e.g. visual information, an audio message, a tactile signal or a combination thereof, encouraging the farmer to further investigate the reasons for the detected deviation in result. In case a plurality of people is working with the herd, a broadcast may be made to the plurality of farmers and their respective associated output units, in some embodiments.

FIG. 3A illustrates a milk analysis apparatus 120 working in conjunction with a milk line/milk extracting arrangement 110. A configuration tag 125 is applied to the milk analysis apparatus 120. The configuration tag 125 comprises a reference sign 115 of the milk extracting arrangement 110. The reference sign 115 is a visual marker such as e.g. an integer, a letter, a geometric shape, a colour, a string of letters, etc.

When the farmer wants to use a certain milk analysis apparatus 120 on a particular milk extracting arrangement 110, he/she may select a configuration tag 125 having an external reference sign 115 corresponding to a visual marker of the milk extracting arrangement 110.

A set of visual markers (e.g. an integer, a letter, a geometric shape, a colour, a string of letters, etc.) corresponding to the visual markers on the reference signs 115 of the configuration tags 125 is provided to the farmer. The farmer may then apply one visual marker on each milk extracting arrangement 110 and thereby baptise it, e.g. to "1", the colour red, "A", etc. Hereby, the farmer is reminded concerning which configuration tag 125 to apply to the milk analysis apparatus 120 when installed to the particular milk extracting arrangement 110, reducing the risk of confusion.

FIG. 3B illustrates the milk analysis apparatus 120 and the configuration tag 125.

The milk analysis apparatus 120 comprises a first wireless communication device 310. The first wireless communication device 310 is configured for wireless communication with a second wireless communication device 320 comprised in the configuration tag 125. The wireless communication between the devices 310, 320 may be made by e.g. Near Field Communication (NFC) communication, Bluetooth, Radio-Frequency Identification (RFID) or other similar short-range wireless communication.

The milk analysis apparatus 120 may also comprise or be associated with a control unit 340 while the configuration tag 125 may comprise a memory device 330 for storage of data. The control unit 340 may optionally be situated outside of the milk analysis apparatus 120 yet being in communicational contact with the first wireless communication device 310.

The control unit 340 of the milk analysis apparatus 120 may thereby obtain information from the configuration tag 125, which is stored in the memory device 330 of the configuration tag 125.

Thus, the control unit 340 of the milk analysis apparatus 120 is configured to retrieve configuration data of the milk extracting arrangement 110 that the milk analysis apparatus 120 is intended to operate in conjunction with, from the memory device 330 of the configuration tag 125 via the first wireless communication device 310. The control unit 340 is also configured to configure the control unit 340, based on the retrieved configuration data of the milk extracting arrangement 110.

The control unit 340 may also be configured to store the obtained information of the configuration tag 125 such as a reference indicator, in a local memory device 350. It thereby becomes possible for the control unit 340 to monitor and detect that the configuration tag 125 has been replaced with another configuration tag 125 dedicated to another milk extracting arrangement 110, which trigger a reconfiguration.

The installation and configuration of the milk analysis apparatus 120 in relation to the milk extracting arrangement 110 is thereby radically facilitated. It also becomes very easy for an farmer to reconfigure the milk analysis apparatus 120 and use it on another milk extracting arrangement 110, just by changing the configuration tag 125 for the milk analysis apparatus 120, wherein the memory device 330 of the configuration tag 125 is preconfigured with an index number or other similar reference to the relevant milk extracting arrangement 110, corresponding to the external reference sign 115 of the configuration tag 125; and/or an IP address of the milk extracting arrangement 110.

The milk analysis apparatus 120 may have a dedicated location wherein the configuration tag 125 is to be fastened during installation, in order for the communication devices 310, 320 to be able to communicate wirelessly with each other. The fastening may be made by an adhesive backside layer on the configuration tag 125; or alternatively by tape, magnetic fastening, snap lock, screw/s, etc. The dedicated location may be indicated by a mark, a descriptive text, a banner, a contour of a graphical shape similar to the shape of the configuration tag 125, etc.

In case of replacing the milk analysis apparatus 120, the configuration tag 125 may be detached and applied to the dedicated location of the replacement milk analysis apparatus 120. Hereby, configuration of the milk analysis apparatus 120 is radically simplified, saving time and efforts of the farmer.

The retrieved configuration data comprises a reference indicator corresponding to the reference sign 115 of the configuration tag 125. The reference indicator is a digital correspondence to the external reference sign 115 of the configuration tag 125. Thus, when the external reference sign 115 is "1", the reference indicator is the integer "1", etc. The reference indicator is stored in the memory device 330 of the configuration tag 125 upon production of the configuration tag 125, thereby ascertaining that the reference indicator is corresponding to the external reference sign 115 of the configuration tag 125.

The control unit 340 may be configured to check whether the retrieved reference indicator corresponds to the milk extracting arrangement 110 to which the milk analysis apparatus 120 currently works in conjunction with. Thus, the control unit 340 may extract a previously stored reference indicator in the local memory device 350 with the currently retrieved reference indicator of the configuration tag 125, stored in the memory device 330 of the configuration tag 125.

When the previously stored reference indicator is not identical with the reference indicator of the configuration tag 125, it means that the configuration tag 125 has been exchanged and thereby also that the farmer wants to associate the milk analysis apparatus 120 with another milk extracting arrangement 110. Thereby, a reconfiguration has to be made. The control unit 340 may then be re-configured to work in conjunction with the milk extracting arrangement 110 as indicated by the retrieved reference indicator of the configuration tag 125.

In the opposite case, i.e. when the previously stored reference indicator is identical with the reference indicator of the configuration tag 125, it means that the same configuration tag 125 is used as the last time the check where made, or alternatively a similar configuration tag 125 having the same external reference sign 115 and reference indicator in the memory device 330. No new configuration is required. The control unit 340 may then be configured to deactivate the first wireless communication device 310 when the reference indicator corresponds to the milk extracting arrangement 110, according to the previously stored reference indicator in the memory device 350.

The control unit 340 may check whether the configuration tag 125 has been changed at a predetermined or configurable time interval, or alternatively at a moment in time just before the milk analysis apparatus 120 is to perform a test session.

It is hereby ascertained that no incertitude is introduced concerning which milk analysis apparatus 120 that is associated with which milk extracting arrangement 110.

The retrieved configuration data may comprise a network location reference such as an IP address, to the milk extracting arrangement 110.

In yet some embodiments, the retrieved configuration data may comprise a network location reference to a data resource 350, from which additional configuration data related to the milk extracting arrangement 110 may be retrievable. Information concerning the reference to the milk extracting arrangement 110, and/or IP address of the milk extracting arrangement 110 may be retrieved from a database, or from a device having another IP address, for example.

The control unit 340 may also be configured to temporarily re-activate the first wireless communication device 310 at a predetermined time interval; and/or to deactivate the first wireless communication device 310 when having retrieved the configuration data from the memory device 330 of the configuration tag 125.

It thereby becomes possible to keep the wireless communication devices 310, 320 activated for as brief period of time as possible. Thereby, transmission disturbance on other wireless communication devices close-by is avoided or at least reduced. Also, energy is saved.

Upon delivery of the milk analysis apparatus 120, the farmer may be provided with a set of configuration tags 125, each preconfigured with configuration data of a milk extracting arrangement 110.

Thereby, the work of the agricultural manager/farmer is further facilitated.

The embodiments, or parts thereof, illustrated in FIG. 1, FIG. 2A, FIG. 2B, FIG. 3A, and/or FIG. 3B may with advantage be combined with each other for achieving further benefits.

The terminology used in the description of the embodiments as illustrated in the accompanying drawings is not intended to be limiting of the described control unit 340, configuration tag 125, dosing module, liquid container 135, cassette 130, milk analysis apparatus 120 and/or system 10. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware but may also be distributed in other forms such as via Internet or other wired or wireless communication system.

The invention claimed is:

1. A control unit of a milk analysis apparatus comprising:
a first wireless communication device, the first wireless communication device being configured for communication with a memory device of a configuration tag that has been applied to the milk analysis apparatus, the configuration tag having a visible reference sign corresponding to a visible identifying marker of a milk extracting arrangement with which said configuration tag is associated, wherein the communication is made via a second wireless communication device comprised in the configuration tag,
wherein the control unit is configured to:
retrieve configuration data of the milk extracting arrangement with which said configuration tag is associated, from the memory device of the configuration tag via the first wireless communication device, the configuration data including a reference indicator corresponding to the reference sign of the configuration tag;
check whether the retrieved reference indicator corresponds to the milk extracting arrangement with which said configuration tag is associated; and
if the retrieved reference indicator corresponds to the milk extracting arrangement with which said configuration tag is associated, deactivate the first wireless communication device.

2. The control unit according to claim 1, wherein the retrieved configuration data comprises a network location reference to the milk extracting arrangement.

3. The control unit according to claim 1, wherein the retrieved configuration data comprises a network location reference to a data resource, from which additional configuration data related to the milk extracting arrangement is retrievable.

4. The control unit of claim 1, wherein if the retrieved reference indicator does not correspond to the milk extracting arrangement with which said configuration tag is associated, the control unit reconfigures itself to work in conjunction with the milk extracting arrangement identified by the retrieved configuration data.

5. The control unit of claim 1, wherein the first and second wireless communication devices communicate with one another via Near Field Communication.

6. The control unit of claim 5, wherein deactivating the first wireless communication device includes de-powering the NFC first wireless communication device.

7. A control unit of a milk analysis apparatus comprising:
a first wireless communication device, the first wireless communication device being configured for communication with a memory device of a configuration tag that has been applied to the milk analysis apparatus, the configuration tag having a visible reference sign corresponding to a visible identifying marker of a milk extracting arrangement with which said configuration tag is associated, wherein the communication is made via a second wireless communication device comprised in the configuration tag,
wherein the control unit is configured to:
activate the first wireless communication device at a predetermined time interval;
retrieve configuration data of the milk extracting arrangement with which said configuration tag is associated, from the memory device of the configuration tag via the first wireless communication device, the configuration data including a reference indicator corresponding to the reference sign of the configuration tag; and
deactivate the first wireless communication device after having retrieved the configuration data.

8. The control unit of claim 7, wherein if the retrieved reference indicator does not correspond to the milk extracting arrangement with which said configuration tag is associated, the control unit reconfigures itself to work in conjunction with the milk extracting arrangement identified by the retrieved configuration data.

9. The control unit of claim 7, wherein the first and second wireless communication devices communicate with one another via Near Field Communication.

10. The system of claim 9, wherein deactivating the first wireless communication device includes de-powering the NFC analysis apparatus wireless communication device.

11. A system comprising:
a plurality of milk extracting arrangements, each having a visible identifying marker;
a plurality of configuration tags, each associated with a respective one of the plurality of milk extracting arrangements, each said configuration tag comprising:
a visible reference sign corresponding to the visible identifying marker of the milk extracting arrangement with which a given said configuration tag is associated;
a memory device in which is stored configuration data including a reference indicator corresponding to the reference sign of the configuration tag; and
a configuration tag wireless communication device; and
at least one configurable milk analysis apparatus, each being structured to attach to any one of the plurality of milk extracting arrangements and perform analysis of milk extracted by the given milk extracting arrangement, each said configurable milk analysis apparatus comprising:
an analysis apparatus wireless communication device; and
a control unit;
wherein each said configuration tag wireless communication device is configured for communication with the control unit of a selected said milk analysis apparatus that is attached to a given one of the plurality of milk extracting arrangements via the analysis apparatus wireless communication device,
wherein the control unit is configured to:
retrieve the configuration data of the given milk extracting arrangement to the control unit of the selected said milk analysis apparatus;
check whether the retrieved reference indicator in the configuration data corresponds to the given milk extracting arrangement; and
if the retrieved reference indicator corresponds to the given milk extracting arrangement, deactivate the analysis apparatus wireless communication device.

12. The system of claim 11, wherein the retrieved configuration data comprises a network location reference to the milk extracting arrangement.

13. The system of claim 11, wherein the retrieved configuration data comprises a network location reference to a data resource from which additional configuration data related to the milk extracting arrangement is retrievable.

14. The system of claim 11, wherein the memory device is configured to provide configuration data comprising a network location reference to the milk extracting arrangement.

15. The system of claim 11, wherein the memory device is configured to provide configuration data comprising a network location reference to a data resource, the data resource comprising additional configuration data related to the milk extracting arrangement and which is retrievable.

16. The system of claim 11, wherein if the retrieved reference indicator does not correspond to the given milk extracting arrangement, the control unit reconfigures itself to work in conjunction with the given milk extracting arrangement identified by the retrieved configuration data.

17. The system of claim 11, wherein the analysis apparatus wireless communication device and the configuration tag wireless communication device communicate with one another via Near Field Communication.

18. The control unit of claim 17, wherein deactivating the first wireless communication device includes de-powering the NFC first wireless communication device.

19. A system comprising:
a plurality of milk extracting arrangements, each having a visible identifying marker;
a plurality of configuration tags, each associated with a respective one of the plurality of milk extracting arrangements, each said configuration tag comprising:
a visible reference sign corresponding to the visible identifying marker of the milk extracting arrangement with which a given said configuration tag is associated;
a memory device in which is stored configuration data including a reference indicator corresponding to the reference sign of the configuration tag; and
a configuration tag wireless communication device; and
at least one configurable milk analysis apparatus, each being structured to attach to any one of the plurality of milk extracting arrangements and perform analysis of milk extracted by the given milk extracting arrangement, each said configurable milk analysis apparatus comprising:
an analysis apparatus wireless communication device; and
a control unit;
wherein each said configuration tag wireless communication device is configured for communication with the control unit of a selected said milk analysis apparatus that is attached to a given one of the plurality of milk extracting arrangements via the analysis apparatus wireless communication device,
wherein the control unit is configured to:
activate the analysis apparatus wireless communication device at a predetermined time interval;
retrieve the configuration data of the given milk extracting arrangement to the control unit of the selected said milk analysis apparatus, the configuration data including a reference indicator corresponding to the reference sign of the configuration tag; and
deactivate the analysis apparatus wireless communication device after retrieving the configuration data.

20. The system of claim 19, wherein if the retrieved reference indicator does not correspond to the given milk extracting arrangement, the control unit reconfigures itself to work in conjunction with the given milk extracting arrangement identified by the retrieved configuration data.

21. The system of claim 19, wherein the analysis apparatus wireless communication device and the configuration tag wireless communication device communicate with one another via Near Field Communication.

22. The system of claim 21, wherein deactivating the first wireless communication device includes de-powering the NFC analysis apparatus wireless communication device.

* * * * *